(12) United States Patent
Shitara et al.

(10) Patent No.: US 6,284,893 B2
(45) Date of Patent: Sep. 4, 2001

(54) PROCESS FOR PRODUCING NITRILE COMPOUNDS

(75) Inventors: Takuji Shitara; Takashi Okawa; Shuji Ebata; Fumisada Kosuge, all of Niigata-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/742,359

(22) Filed: Dec. 22, 2000

(30) Foreign Application Priority Data

Dec. 27, 1999 (JP) .................................................. 11-369773
Apr. 4, 2000 (JP) .................................................. 12-101971

(51) Int. Cl.$^7$ ........................ C07C 253/28; C07D 211/84
(52) U.S. Cl. .......................... 546/286; 558/309; 558/328
(58) Field of Search .................... 558/309, 328; 546/286

(56) References Cited

U.S. PATENT DOCUMENTS

| | | | | |
|---|---|---|---|---|
| 3,079,422 | * | 2/1963 | Pasky et al. | 260/465 |
| 3,462,476 | * | 8/1969 | O'Donnel et al. | 260/465 |
| 3,594,987 | * | 7/1971 | Oa et al. | 55/53 |
| 4,055,587 | * | 10/1977 | Norton et al. | 260/465 |
| 5,892,049 | * | 6/1999 | Hippel et al. | 546/286 |
| 6,057,471 | * | 5/2000 | Nakamura et al. | 558/321 |
| 6,107,510 | * | 8/2000 | Ebata et al. | 558/327 |
| 6,187,943 | * | 2/2001 | Sasaki et al. | 558/318 |

OTHER PUBLICATIONS

Morgan C. Sze, Hydrocarbon Processing, Feb. 1976, 103–106.*

* cited by examiner

Primary Examiner—Joseph K. McKane
Assistant Examiner—Kamal Saeed
(74) Attorney, Agent, or Firm—Antonelli, Terry, Stout, & Kraus, LLP (57) ABSTRACT

There is disclosed a process for producing a nitrile compounds by ammoxidation of a carbocyclic or heterocyclic compound having organic substituent(s) by reacting the compound with ammonia and an oxygen-containing gas, wherein unreacted ammonia is recovered from the reaction product gas and recycled to the reaction system.

11 Claims, 1 Drawing Sheet

Fig. 1

PROCESS FOR PRODUCING NITRILE COMPOUNDS

BACKGROUND OF THE INVENTION

1. Field of the Invention

The present invention relates to a process for producing carbocyclic nitriles or heterocyclic nitrites (hereinafter commonly referred to as "nitrile compounds") by reacting a carbocyclic or heterocyclic compound having organic substituent(s), with ammonia and an oxygen-containing gas. More particularly, the invention relates to a process in which unreacted ammonia is recovered from the reaction product gas and recycled to the reaction system.

Carbocyclic nitriles are useful as raw materials for the production of synthetic resins, agricultural chemicals or the like, or as intermediate products of amines, isocyanates or the like. Also, heterocyclic nitrites are useful as intermediate products of medicines, feed additives, food additives or the like.

2. Description of the Prior Art

The nitrile compounds have been produced by reacting a hydrocarbon compound with ammonia and a oxygen-containing mixed gas, i.e., by so-called ammoxidation. When carbocyclic or heterocyclic nitrites are synthesized by ammoxidation of corresponding carbocyclic or heterocyclic compounds having organic substituent(s), a large amount of heat is generated as compared to ammoxidation of olefins. Accordingly, the ammoxidation of carbocyclic or heterocyclic compounds is advantageously carried out by vapor-phase fluid catalytic reaction to facilitate removal of the reaction heat and avoid the occurrence of side reactions due to local heating.

As catalysts for the vapor-phase fluid catalytic reaction, there have been proposed various catalyst systems comprising a metal oxide which may or may not be supported on a carrier such as silica and alumina. For example, Japanese Patent Publication No. 49-45860 discloses a process for producing aromatic nitriles by subjecting alkyl-substituted aromatic compounds to ammoxidation. Japanese Patent Application Laid-Open No. 63-190646 discloses a process for the ammoxidation of alkyl-substituted aromatic compounds or alkyl-substituted alicyclic compounds using Fe/Sb-based catalysts.

Also, Japanese Patent Application Laid-Open No. 1-275551 discloses a process for the ammoxidation of alkyl-substituted aromatic compounds or alkyl-substituted alicyclic compounds using V/Cr/B/Mo-based catalysts. Japanese Patent Application Laid-Open No. 5-170724 discloses the similar process using Mo/P-based catalysts. Japanese Patent Application Laid-Open No. 9-71561 discloses a process for the production of dicyanobenzene by ammoxidation of xylene using Fe/Sb/V-based catalysts.

In these ammoxidation reactions, ammonia is used in an excessive amount relative to stoichiometric amount thereof in order to produce respective nitrites corresponding to the alkyl-substituted aromatic compounds and alkyl-substituted alicyclic compounds at a high yield. Usually, the ammonia is used in an amount of 3 to 7 moles per mole of one organic substituent contained in the raw material. In industrial-scale operations, from economical viewpoint, unreacted ammonia is preferably recovered from the reaction gas and recycled to the reaction system.

There have been conventionally proposed various processes in which after separating nitrile compounds from the ammoxidation reaction product gas, unreacted ammonia is recovered from the residual gas and recycled to the reaction system.

In "Monthly Report of Japan Chemical Society", vol. 22, pp. 419–451 (1972), there is disclosed the process for producing isophthalonitrile by the ammoxidation of m-xylene wherein unreacted ammonia is recovered from the reaction product gas after separating the isophthalonitrile therefrom and recycled to the reaction system, and the residual waste gas is converted into harmless state, and discharged.

In addition, "Chemical Process Collection" (edited by Institute of Chemical Engineering; pp. 749–752) discloses the process for the production of benzonitrile. In this process, toluene, ammonia and air are subjected to ammoxidation in the presence of a Mn/W-based catalyst by fixed bed method. The reaction product gas is cooled to 10° C. or lower to collect benzonitrile and water. Then, the residual gas is introduced into an ammonia recovering tower and separated into waste gases (carbon dioxide gas, carbon monoxide, nitrogen, oxygen, etc.) and ammonia. The thus recovered ammonia is recycled to the reaction system. The liquid collected by cooling is separated into a water phase and an organic phase containing benzonitrile, and then the organic phase is introduced into a distillation tower where the organic phase is separated into low boiling substances (such as unreacted toluene, ammonia, hydrogen cyanide, water, etc.) and crude benzonitrile. Further, the crude benzonitrile is introduced into a purification tower, and separated into benzonitrile and high boiling substances.

In the above process, the reaction product gas is cooled to collect the liquid containing benzonitrile, and then only ammonia recovered from the residual gas is recycled to the reaction system. However, in this process, since the reaction product gas is cooled to 10° C. or lower, the collected liquid inevitably contains large amounts of ammonia and ammonium carbonate, thereby failing to recover ammonia contained in the liquid. "Hydrocarbon Processing", pp. 103–106, (February, 1976) discloses the process for producing aromatic nitrites by conducting the ammoxidation in the presence of a metal oxide catalyst by vapor-phase fluid catalytic reaction. In this process, after the reaction product gas is cooled in a cooler to collect the nitrile compounds therefrom, the residual gas is introduced into an absorption tower where unreacted ammonia and by-produced hydrogen cyanide are dissolved in water to separate these compounds from waste gases (carbon monoxide, nitrogen, etc.). The thus obtained aqueous solution is then introduced into a diffusion tower and separated into waste liquid containing high boiling substances and a fraction containing ammonia, hydrogen cyanide, water or the like. The fraction is further introduced into a distillation tower and separated into ammonia and an aqueous solution (containing hydrogen cyanide and ammonium carbonate). Then, the aqueous solution is separated into a mixture of hydrogen cyanide and a carbon dioxide gas, and ammonia-containing water. The ammonia-containing water is returned to the preceding distillation tower. The nitrile compounds collected by cooling is separately purified.

Thus, in the above process, after separating the nitrile compounds from the reaction product gas, only ammonia recovered from the residual gas is recycled to the reaction system. For this reason, this process is more advantageous as compared to the previous benzonitrile production process because ammonia contained in ammonium carbonate can also be recovered. However, in this process, the use of additional facilities such as diffusion tower, distillation tower and ammonium carbonate-decomposition tower is required to separate ammonia and hydrogen cyanide (containing carbon dioxide) from the residual gas, resulting in increased costs for facilities.

In "Chemical Engineering", pp. 53–55 (November, 1971), there is disclosed the process for the production of isophthalonitrile. In this process, m-xylene, ammonia and air are subjected to ammoxidation using a vanadium oxide catalyst by fixed bed reaction. The reaction product gas is introduced into a scrubber and water-cooled therein to crystallize isophthalonitrile. The residual gas is further introduced into an absorption tower where unreacted ammonia and by-produced hydrogen cyanide are dissolved in water, and the waste gas discharged from the top of the tower is burned for disposal. In the above document, it is described to recover ammonia from the aqueous solutions produced in the scrubber and absorption tower and recycled the recovered ammonia to the reaction system. However, no concrete method therefor is specified therein. The isophthalonitrile-containing water slurry condensed in the scrubber is introduced into a filter to separate isophthalonitrile therefrom, and the separated isophthalonitrile is then dehydrated and dried to obtain the aimed product.

When carbocyclic or heterocyclic compounds having organic substituent(s) are reacted with ammonia and an oxygen-containing gas such as air, the reaction product gas contains unreacted carbocyclic or heterocyclic compounds, nitrile compounds, ammonia, hydrogen cyanide, a carbon dioxide gas, water, carbon monoxide, nitrogen, oxygen and the like. Usually, the reaction product gas contains the by-produced hydrogen cyanide at a concentration of about 1%. The by-produced hydrogen cyanide is readily converted into formamide, polymers or the like due to heat history, and the thus produced compounds are contained in waste water, thereby increasing a total oxygen demand (TOD) of the waste water and causing coloration thereof. Also, when the reaction product gas is cooled, carbon dioxide contained in the gas is readily precipitated as ammonium carbonate. Therefore, in the above process for the production of carbocyclic or heterocyclic nitrites, when nitrile compounds are removed from the reaction product gas and then unreacted ammonia is recovered from the residual gas, it is important not only to avoid operational troubles of apparatuses due to the conversion of hydrogen cyanide and precipitation of ammonium carbonate, but also to reduce the burden for treating the waste water and increase a recovery rate of unreacted ammonia.

Thus, in the conventional processes described in the above prior arts, after separating nitrile compounds from the reaction product gas, only ammonia recovered from the residual gas is recycled to the reaction system. Therefore, the recovery rate of ammonia is low. The by-produced hydrogen cyanide is burned, or otherwise converted into polymers or the like and contained in the waste water. In addition, in order to separate ammonia from hydrogen cyanide, it is required to use additional facilities such as distillation tower and ammonium carbonate decomposition tower, resulting in increased installation costs for facilities.

The present inventors have studied the recovery of ammonia upon the production of isophthalonitrile by ammoxidation of m-xylene. As a result, it has been found that when fresh ammonia is used as a raw material, the aimed nitrile compounds is produced at a high yield and the activity of catalyst used is prevented from being deteriorated with time, but when ammonia recovered by the above processes is used, the ammoxidation reaction is inhibited, so that the amount of nitrile compounds as the aimed product is reduced, and the activity of the catalyst is considerably deteriorated due to promoted sintering, thereby failing to stably obtain the aimed product for a long period of time.

SUMMARY OF THE INVENTION

A first object of the present invention is to provide an economically advantageous process for producing carbocyclic or heterocyclic nitrile by the ammoxidation of a corresponding carbocyclic or heterocyclic compound by vapors-phase fluid catalytic reaction, wherein the aimed product can be stably obtained at a high yield for a long period of time while recovering unreacted ammonia from the reaction gas and recycling the recovered ammonia to the reaction system.

A second object of the present invention is to provide a process for producing the nitrile compounds by the same ammoxidation as described above, wherein after separating the nitrile compounds from the reaction product gas, unreacted ammonia, etc., can be effectively recovered from the residual gas and recycled to the reaction system, thereby not only reducing costs required for treatment of wastes or the like, but also stably obtaining the aimed product for a long period of time.

As a result of further extensive researches in view of the above first object, concerning the process in which the ammoxidation is conducted using a known catalyst containing vanadium, molybdenum, iron or the like and unreacted ammonia is recovered from the reaction gas and recycled to the reaction system, the present inventors have found that the deterioration in activity of the catalyst is caused by the water contained in the recovered ammonia, and the aimed product is stably produced at a high yield for a long period of time by controlling the water content of recovered ammonia to a specific range by distillation method to maintain the water content of gas supplied to a reactor at a predetermined level.

Namely, in a first aspect of the present invention, there is provided a process for producing a nitrile compounds by reacting a carbocyclic or heterocyclic compound having organic substituent(s) with ammonia and an oxygen-containing gas, which comprises the steps of conducting vapor-phase catalytic ammoxidation of the carbocyclic or heterocyclic compound in the presence of a fluid catalyst containing at least one metal oxide selected from the group consisting of vanadium oxide, molybdenum oxide and iron oxide while controlling a water content of gas supplied to a reactor to 12% by volume or lower; recovering unreacted ammonia from the reaction product gas; and recycling the recovered ammonia to reaction system.

Further, as a result of extensive researches in view of the above second object, the present inventors have found that after separating the nitrile compounds from the reaction product gas, when unreacted ammonia, by-produced hydrogen cyanide and ammonium carbonate contained in the residual gas are dissolved in water and the obtained aqueous solution is distilled under specific conditions, it is possible to efficiently recover ammonia and hydrogen cyanide at the same time, and when the recovered ammonia is recycled to the reaction system, it is possible to not only reduce costs required for treatment of wastes or the like, but also stably obtain the aimed nitrile compounds at a high yield for a long period of time.

Namely, in a second aspect of the present invention, there is provided a process for producing a nitrile compounds by reacting a carbocyclic or heterocyclic compound having organic substituent(s) with ammonia and an oxygen-containing gas, which comprises the steps of separating the nitrile compounds from the reaction product gas; absorbing unreacted ammonia and by-produced hydrogen cyanide contained in the residual gas, in water; distilling the obtained solution under a pressure of 0.2 to 0.7 MPa to recover ammonia and hydrogen cyanide therefrom; and recycling the recovered ammonia and hydrogen cyanide to the reaction system.

DESCRIPTION OF PREFERRED EMBODIMENTS

Examples of the carbocyclic compounds having organic substituent(s) which are used as a raw material in the present invention, include those compounds having a carbon ring such as benzene, naphthalene, anthracene, cyclohexene, cyclohexane, dihydronaphthalene, tetralin and decalin, and containing as side chains, organic substituent(s) bonded to the carbon ring such as methyl, ethyl, propyl, formyl, acetyl, hydroxymethyl, methoxycarbonyl and alkoxyl. The carbocyclic compounds may further contain inorganic substituent(s) such as halogen, hydroxyl, amino and nitro. Specific examples of the carbocyclic compounds having organic substituent(s) include toluene, xylene, trimethyl benzene, ethyl benzene, methyl naphthalene, dimethyl naphthalene, methyl tetralin, dimethyl tetrain, chlorotoluene, dichlorotoluene, methyl amyrin, cresol and methyl anisole.

Examples of the heterocyclic compounds having organic substituent(s) which are used as a raw material in the present invention, include those compounds having a hetero ring such as furan, pyrrole, indole, thiophene, pyrazole, imidazole, oxazole, pyran, pyridine, quinoline, isoquinoline, pyrroline, pyrrolidine, imidozoline, imidazoline, piperidine and piperazine, and containing the above organic substituent (s) bonded to the hetero ring. The heterocyclic compounds may also contain as side chains, the same inorganic substituent(s) as described with respect to the above carbocyclic compounds. Specific examples of the heterocyclic compounds having organic substituent(s) include furfural, 2-methyl thiophene, 3-methyl thiophene, 2-formyl thiophene, 4-methyl thiazole, methyl pyridine, dimethyl pyridine, trimethyl pyridine, methyl quinoline, methyl pyrazine, dimethyl pyrazine, methyl piperazine or the like.

These carbocyclic or heterocyclic compounds may be used singly or in the form of a mixture of any two or more thereof.

The ammoxidation is conducted by vapor-phase fluid catalytic reaction in order to obtain a uniform temperature distribution. In the ammoxidation, there is suitably used a catalyst comprising as essential component, at least one metal oxide selected from the group consisting of vanadium oxide, molybdenum oxide and iron oxide. Further, such a catalyst composed of a plurality of metal oxides which is modified by adding an oxide of at least one element selected from the group consisting of Mg, Ca, Ba, La, Ti, Zr, Cr, W, Co, Ni, B, Al, Ge, Sn, Pb, P, Sb, Bi, Li, Na, K, Rb and Cs to the above metal oxide, may be used in order to enhance the activity, strength (wear resistance) and life thereof. The latter catalyst is represented by the following composition formula:

$$(V)_a(MO)_b(Fe)_c(X)_d(Y)_e(O)_f$$

wherein X is at least one element selected from the group consisting of Mg, Ca, Ba, La, Ti, Zr, Cr, W, Co and Ni; Y is at least one element selected from the group consisting of B, Al, Ge, Sn, Pb, P, Sb, Li, Na, K, Rb and Cs; and subscripts a to f represent atomic ratios of respective elements with the proviso that a is 0.01 to 1 (preferably 0.1 to 0.7), b is 0.01 to 1 (preferably 0.05 to 0.7), c is 0 to 1 (preferably 0.05 to 0.7), d is 0 to 1 (preferably 0.05 to 0.7), e is 0 to 1 (preferably 0.05 to 0.7), and f is the number of oxygen atoms in the oxide obtained by bonding the above elements thereto.

Of the catalysts represented by the above composition formula, especially preferred catalysts are those composed of metal oxides containing V, Cr, B, Mo and P together with an alkali metal such as Na or K.

Examples of the vanadium sources include inorganic salts such as ammonium salt and sulfate, and vanadium salts of organic acids such as oxalic acid and tartaric acid. Examples of the chromium sources include chromic acid, chromium nitrate, chromium hydroxide, ammonium chromate, ammonium bichromate, and chromium salts of organic acids such as oxalic acid and tartaric acid. Examples of the boron sources include boric acid and ammonium borate. Examples of the molybdenum sources include ammonium molybdate, phosphomolybdic acid, ammonium phosphomolybdate, and molybdenum salts of organic acids such as oxalic acid and tartaric acid. Examples of the phosphorus sources include phosphomolybdic acid and ammonium phosphomolybdate as described above. Examples of the alkali metal sources include Li, Na, K, Rb and Cs, especially hydroxides, carbonates or nitrates of Na or K, and alkali metal salts of organic acids such as oxalic acid, tartaric acid and acetic acid. In addition, as raw materials of the catalysts, there may also be used metal salts of inorganic acids or organic acids capable of readily forming oxides by heating these salts in air.

The above catalysts used in the present invention may be suitably supported on any known carrier such as silica and alumina, especially silica. As the silica carrier, there may be used silica gel, colloidal silica and anhydrous silica described, for example, in "CHEMICAL HANDBOOK-APPLIED CHEMISTRY" published by Maruzen, pp. 256–258 (1986). When the silica carrier contains alkali metal, the amount of alkali metal must be taken into consideration upon the preparation of the catalyst. The amount of the silica carrier used is in the range of 20 to 80% by weight, preferably 40 to 70% by weight based on the weight of the catalyst.

These catalysts may be produced by known methods. For example, when the catalyst is prepared by supporting V/Cr/B/Mo/P/Na-containing metal oxides on the silica carrier, a boric acid solution and sodium acetate are added to a solution prepared by dissolving vanadium oxide and chromium oxide in oxalic acid, and then silica gel is added to the resultant solution to obtain a slurried mixture. In this case, any solubilizing agent may be used to facilitate dissolution of boric acid, if required. Examples of the solubilizing agent for boric acid include polyhydric alcohols, α-monooxycarboxylic acids and dioxycarboxylic acids. In the preparation of fluid catalysts, the obtained mixture is spray-dried and, if required, further dried at a temperature of 110 to 150° C. Then, the obtained dried catalyst is calcined. The calcination may be conducted at a temperature of 400 to 700° C., preferably 450 to 650° C. for several or more hours while passing air therethrough. Meanwhile, it is preferred that pre-calcination is conducted prior to the above substantial calcination.

The catalyst used in the present invention has a particle size of 10 to 300 μm; an average particle size of 30 to 200 μm, preferably 40 to 100 μm; and a bulk density of 0.5 to 2 g/cm³, preferably 0.7 to 1.5 g/cm³.

The suitable oxygen-containing gas used in the ammoxidation is usually air which may be in oxygen-rich state.

Further, the oxygen-containing gas may be used in combination with a diluent such as nitrogen and a carbon dioxide gas. The amount of oxygen used is 1.5 moles or higher, preferably 2 to 50 moles per mole of one organic substituent contained in the carbocyclic or heterocyclic compound. When the amount of oxygen used is less than 1.5 moles, the yield of the aimed nitrile compounds is lowered. On the other hand, when the amount of oxygen used is more than 50 moles, the space time yield of the aimed nitrile compounds is reduced.

When air is used as the oxygen-containing gas in the ammoxidation, the concentration of the carbocyclic or heterocyclic compound contained in a raw gas supplied to a reactor is 0.2 to 10% by volume, preferably 0.5 to 5% by volume. When the concentration of the carbocyclic or heterocyclic compound is more than 10% by volume, the yield of the aimed nitrile compounds is lowered. On the other hand, when the concentration of the carbocyclic or heterocyclic compound is less than 0.2% by volume, the space time yield of the aimed nitrile compounds is reduced.

The ammonia used as raw material may be industrial-grade ones. The amount of ammonia used is 1 to 10 moles, preferably 3 to 7 moles per mole of one organic substituent contained in the carbocyclic or heterocyclic compound. When the amount of ammonia used is less than 1 mole, the yield of the aimed nitrile compounds is lowered. On the other hand, when the amount of ammonia used is more than 10 moles, the space time yield of the aimed nitrile compounds is reduced.

As described above, the present inventors have found that water contained in the unreacted ammonia recycled adversely affects the activity of the catalyst. The water concentration in feed gas supplied to a reactor is 12% by volume or lower, preferably 10% by volume or lower. When the water concentration is more than 12% by volume, the yield of the aimed nitrile compounds is lowered, and the activity of the catalyst is deteriorated due to promoted sintering thereof, thereby failing to stably obtain the aimed nitrile compounds for a long period of time.

In the present invention, the ammoxidation is preferably performed using a fluidized bed reactor. Various types of fluidized bed reactors may be used in the process of the present invention. Ammonia may be fed into the reactor in the form of a mixture with the carbocyclic or heterocyclic compound. Alternatively, ammonia and the carbocyclic or heterocyclic compound may be separately fed into the reactor. Further, a mixture of ammonia, the carbocyclic or heterocyclic compound and a part of the oxygen-containing gas may be fed into the reactor.

The ammoxidation may be conducted at a temperature of 300 to 500° C., preferably 330 to 470° C. When the ammoxidation temperature is less than 300° C., the conversion rate of the reactants is lowered. On the contrary, when the ammoxidation temperature is more than 500° C., the amounts of by-produced carbon dioxide gas and hydrogen cyanide are increased, resulting in poor yield of the aimed nitrile compounds. Also, the ammoxidation may be performed under either ordinary, increased or reduced pressure, but preferably under a pressure ranging from about ordinary pressure to 0.2 MPa. The time of contact between the reactant gas and the catalyst varies depending upon kind of raw material, molar ratios of ammonia and the oxygen-containing gas charged based on the raw material, the ammoxidation temperature or the like. The contact time is usually in the range of 0.5 to 30 seconds.

As described above, as to the first aspect of the present invention, the present inventors have found that water contained in the unreacted ammonia recycled adversely affects the activity of the catalyst. The water concentration of the gas fed to the reactor is 12% by volume or lower, preferably 10% by volume or lower. When the water concentration is more than 12% by volume, the yield of the nitrile compounds is lowered, and the activity of the catalyst is considerably deteriorated due to promoted sintering, thereby failing to stably obtain the aimed nitrile compounds for a long period of time.

Since a larger part of water in the gas fed to the reactor is contained in the recovered ammonia, the amount of water in the gas fed to the reactor can be optimized by controlling the water content of the recovered ammonia. The water content of the recovered ammonia is controllable by varying distillation conditions, and is usually 30% by volume or lower, preferably 5 to 20% by volume. Even when the water content of the recovered ammonia is less than 5% by volume, the yield of the aimed product is not deteriorated. However, large costs are required for purifying the recovered ammonia to such a level, resulting in economically disadvantageous process.

Thus, in the first aspect of the present invention, the carbocyclic or heterocyclic compound is ammoxidized by vapor-phase fluid catalytic reaction using the catalyst containing at least one metal oxide selected from the group consisting of vanadium oxide, molybdenum oxide and iron oxide, and then unreacted ammonia is recovered from the reaction gas and recycled to the reaction system. In this case, by controlling the water concentration in the gas fed to a reactor to 12% by volume or lower, it is possible to stably obtain the nitrile compounds at a high yield for a long period of time.

Further, according to the first aspect of the present invention, since unreacted ammonia is recovered from the ammoxidation reaction product gas and usefully reused, the amount of ammonia used as raw material is considerably reduced, so that the production of carbocyclic or heterocyclic nitrites is conducted in an industrially advantageous manner.

Figure 1:
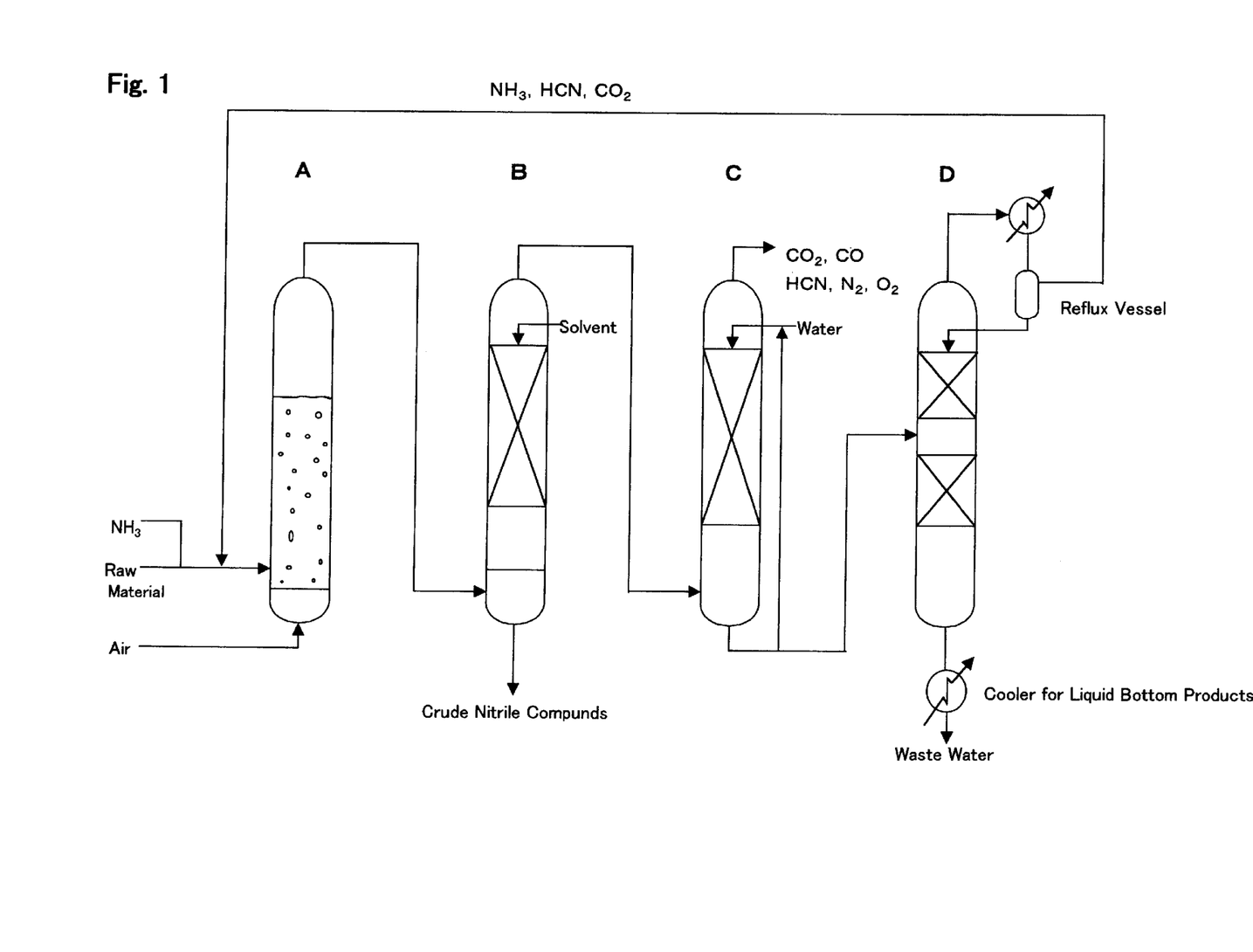
FIG. 1 is a flow diagram of an apparatus for the production of nitrile compounds by ammoxidation showing an embodiment of the second aspect of the present invention, wherein A is an ammoxidation reactor; B is a nitrile separation tower; C is an ammonia absorption tower; and D is an ammonia regeneration tower.

Then, the process of separating the nitrile compounds from the reaction product gas at an outlet of the reactor, recovering unreacted ammonia from the residual gas and then recycling the recovered ammonia to the reaction system in accordance with the second aspect of the present invention, will be explained below. FIG. 1 is a flow diagram showing an embodiment of the second aspect of the present invention. However, the flow diagram of FIG. 1 is not intended to limit the present invention thereto.

In FIG. 1, there is shown an ammoxidation reactor A packed with the catalyst. The reactor is of a fluidized bed type in which air is fed from the bottom thereof. Ammonia and a carbocyclic or heterocyclic compound are fed from a lower portion of the catalyst layer. The reaction product gas discharged from a top of the reactor, contains unreacted carbocyclic or heterocyclic compound, nitrile compounds, ammonia, hydrogen cyanide, carbon dioxide gas, water, carbon monoxide, nitrogen, oxygen and the like.

The reaction product gas is introduced into a nitrile separation tower B where the gas is contacted with a solvent so that the nitrile compounds is dissolved therein and separated from the reaction product gas. As the solvent, there may be used various organic solvents or water, preferably organic solvents which have a higher boiling point than that of the raw carbocyclic or heterocyclic compound and a high dissolution power to the nitrile compounds, and are inert to the nitrile compounds. When the boiling point of the solvent is low, the amount of the solvent entrained on the residual gas is increased.

Specific examples of the organic solvents include aliphatic hydrocarbons such as octane, nonane and decane, and aromatic hydrocarbons such as toluene, xylene and mesitylene. The aliphatic or aromatic hydrocarbons may contain in a molecule thereof, at least one substituent selected from the group consisting of alkyl, hydroxyl, amide, halogen, alkoxyl, amino, nitro and nitrile. Examples of such substituted aliphatic or aromatic hydrocarbons include ethyl benzene, cresol, chlorobenzene, dichlorobenzene, dimethylsulfoamide, methylanisole, nitrobenzene, benzonitrile, methylbenzonitrile or the like.

The temperature of the nitrile separation tower B varies depending upon kind of solvent used, and is usually not more than boiling point of the solvent. The pressure within the nitrile separation tower B may be either ordinary, increased or reduced pressure, and is preferably in the range between ordinary pressure and the reaction pressure.

Alternatively, the nitrile compounds may be recovered in the form of crystals from the reaction gas by using a cooler instead of the separation tower. The crude nitrile compounds collected by these processes may be further subjected to purification treatments such as distillation and recrystallization to recover a high-purity nitrile compounds.

The gas from which the nitrile compounds is separated, i.e., the residual gas discharged from the top of the nitrile separation tower B, is then introduced into an ammonia absorption tower C having trays or packed beds where unreacted ammonia, by-produced hydrogen cyanide, ammonium carbonate, etc., are dissolved in water. The temperature of the ammonia absorption tower C is not more than boiling point of water, and the pressure thereof is preferably in the range of from ordinary pressure to the operating pressure of the nitrile separation tower B. The waste gas discharged from the ammonia absorption tower C, usually contains non-condensed or undissolved carbon dioxide gas, carbon monoxide, nitrogen, oxygen, hydrogen cyanide or the like, and is burned for disposal.

The aqueous solution discharged from the ammonia absorption tower C is introduced into an ammonia regeneration tower D where ammonia is recovered by distillation. As the ammonia regeneration tower D, there may be used a tray tower, a packed tower or the like. At the top of the ammonia regeneration tower D, ammonia and hydrogen cyanide as well as ammonia and a carbon dioxide gas produced by decomposition of ammonium carbonate are recovered at the same time, and then directly recycled to the reaction system. On the other hand, from the bottom of the ammonia regeneration tower D, an aqueous solution containing a high-boiling components are discharged and treated as liquid wastes.

The operating pressure of the ammonia regeneration tower D is in the range of 0.2 to 0.7 MPa, preferably 0.2 to 0.5 MPa. The temperature of the ammonia regeneration tower D varies depending upon the operating pressure. When the operating pressure is out of the above-specified range, it is difficult to stably operate the ammonia regeneration tower D for a long period of time due to the occurrence of various problems in the regeneration tower. If a mixed gas containing the recovered ammonia out of the above-specified range is recycled to the reaction system, the ammoxidation reaction is adversely affected.

More specifically, when the operating pressure of the ammonia regeneration tower D is more than 0.7 MPa, the amount of by-products derived from hydrogen cyanide is increased. As a result, the operating performance is lowered due to foaming, flooding or sticking of high-boiling substances onto heat exchanger. Further, the waste water is colored, and the TOD thereof is considerably increased.

When the operating pressure is less than 0.2 MPa, the dew point of stream at the top of the tower is lowered, resulting in precipitation of ammonium carbonate. As a result, stable operation of the ammonia regeneration tower D becomes difficult. In addition, the water content of the mixed gas containing the recovered ammonia is increased. Therefore, when the mixed gas is directly recycled to the reaction system, the yield of the nitrile compounds is lowered, and the activity of the catalyst is considerably deteriorated due to promoted sintering thereof, thereby failing to stably obtain the aimed nitrile compounds for a long period of time. Alternatively, before being recycled to the reaction system, the gas circulated from the top of the regeneration tower may be distilled or passed through a dehydration tower filled with dehydrating agent, in order to reduce the water content thereof.

The reflux ratio of the ammonia regeneration tower D is 0.1 to 2.0, preferably 0.2 to 1.5. In the distillation procedure, the liquid residence time in the ammonia regeneration tower D constituted by the regeneration tower, condenser, reboiler, reflux vessel, etc., is in the range of 0.1 to 2.0 hours, preferably 0.1 to 0.5 hour in order to inhibit the production of high-boiling substances derived from hydrogen cyanide. Meanwhile, the liquid residence time is given by a sum of an upper liquid residence time calculated from reflux amount ($m^3$/h) relative to hold-up amount ($m^3$) in condenser, reflux vessel and an upper portion (concentration portion) of the regeneration tower, and a lower liquid residence time calculated from a total amount ($m^3$/h) of feed liquid amount and reflux amount relative to hold-up amount ($m^3$) in reboiler and a lower portion (recovery portion) of the regeneration tower.

When the mixed gas containing the recovered ammonia is recycled to the reaction system while keeping the above operating conditions of the ammonia regeneration tower D, the concentration of hydrogen cyanide in the reaction system is kept in equilibrium state at a constant level. The hydrogen cyanide is discharged from the top of the ammonia absorption tower C in an amount corresponding to the amount by-produced in the ammoxidation reaction, together with the waste gas, or discharged after being converted into formamide, ammonium formate, etc. by hydrolysis thereof at the bottom of the ammonia regeneration tower.

In the process of the present invention, after separating the nitrile compounds from the reaction product gas of the ammoxidation, unreacted ammonia and the like are absorbed into water, and then the obtained solution is distilled under the specific conditions to recover ammonia therefrom. In this case, although ammonia, hydrogen cyanide and a carbon dioxide gas are introduced into the ammoxidation reactor, substantially no deterioration in activity of the catalyst is observed upon recycling the recovered ammonia to the reactor, so that the nitrile compounds can be stably obtained for a long period of time. Also, in the present process, the recovery of ammonia is readily performed only by using absorption and distillation towers, resulting in economically advantageous process. Further, the amount of hydrogen cyanide decomposed at the ammonia regeneration tower is reduced by circulating hydrogen cyanide or the like to the ammoxidation reactor, so that the load for treatment of waste water discharged from the bottom of the regeneration tower is considerably reduced.

The present invention will be described in more detail by reference to the following examples. However, it should be noted that the following examples are illustrative and not intended to limit the invention thereto.

Meanwhile, in EXAMPLES 7, 8 and 9 as well as COMPARATIVE EXAMPLE 6 concerning the second aspect of the present invention, the degree of coloration of liquid bottom products at the ammonia regeneration tower was measured by Gardner color scale (JIS K-0071-2).

Preparation of Catalyst A:

Five hundreds milliliters of water was added to 229 g of vanadium pentaoxide ($V_2O_5$), and the resultant mixture was heated to 80 to 90° C. Then, 477 g of oxalic acid was added to the mixture while intimately stirring to dissolve solids therein. Separately, 400 ml of water was added to 963 g of oxalic acid, and the resultant mixture was heated to 50 to 60° C. Then, the mixture was mixed with a solution prepared by adding 252 g of chromic anhydride ($CrO_3$) to 200 ml of water, while intimately stirring to dissolve solids therein. The thus obtained vanadyl oxalate solution and chromium oxalate solution were mixed together at a temperature of 50 to 60° C. to obtain a vanadium/chromium-containing solution. Then, the thus obtained vanadium/chromium-containing solution was mixed with a solution prepared by dissolving 41.1 g of phosphomolybdic acid ($H_3[PMo_{12}O_{40}] \cdot 20H_2O$) in 100 ml of water, and further with a solution prepared by dissolving 4.0 g of potassium acetate ($CH_3COOK$) in 100 ml of water. Then, 2,500 g of 20 wt % aqueous silica sol (containing 0.02% by weight of $Na_2O$) was added to the mixed solution. The resultant slurry was intimately mixed with 78 g of boric acid ($H_3BO_3$), and then concentrated by heating until the liquid amount was reduced to about 3,800 g. The obtained catalyst solution was spray-dried while maintaining the inlet temperature at 250° C. and the outlet temperature at 130° C. The spray-dried catalyst was further dried by a dryer maintained at 130° C. for 12 hours, pre-calcined at 400° C. for 5 hours, and then calcined at 550° C. for 8 hours under air stream. The thus obtained fluid catalyst contained as catalyst components, V, Cr, B, Mo, P, Na and K in such amounts that the atomic ratio of V:Cr:B:Mo:P:Na:K was 1:1:0.5:0.086:0.007:0.009:0.020. The concentration of these catalyst components in the fluid catalyst is 50% by weight. The fluid catalyst was hereinafter referred to as "catalyst A".

EXAMPLE 1

A 23 mmφ reactor heated by a resistance heating element was charged with 40 ml of the catalyst A. Then, a mixed gas composed of 3.2% by volume of m-xylene 71.3% by volume of air and 25.5% by volume of recovered ammonia containing 5.0% by volume of water, was fed to the reactor, and then subjected to fluid catalytic reaction at a space velocity (SV) of 850 $Hr^{-1}$ and a temperature of 420° C. at which the maximum yield of isophthalonitrile was expected when using the catalyst A. The water content of the mixed gas fed to the reactor was 1.3% by volume. As a result of the reaction, it was confirmed that the initial yield of isophthalonitrile based on m-xylene was 86.4 mol %. Then, the reaction was continued at 450° C. for 300 hours for applying a heat load to the reaction system, and then conducted again at 420° C. in the same manner as described above. It was confirmed that the yield of isophthalonitrile was still as high as 85.9 mol % after bearing heat load. Accordingly, it was recognized that when the recovered ammonia having a well-controlled water content was fed to the reaction system, the aimed product was stably produced at a high yield without change with time.

EXAMPLE 2

A mixed gas composed of 2.9% by volume of m-xylene, 64.8% by volume of air and 32.3% by volume of recovered ammonia containing 25.0% by volume of water vapor, was charged into a reactor packed with the catalyst A, and then subjected to fluid catalytic reaction at a space velocity (SV) of 850 $Hr^{-1}$ and a temperature of 420° C. at which the maximum yield of isophthalonitrile was expected when using the catalyst A. The water content of the mixed gas fed to the reactor was 8.1% by volume. As a result of the reaction, it was confirmed that the initial yield of isophthalonitrile based on m-xylene was 85.2 mol %. Then, the reaction was continued at 450° C. for 300 hours for applying a heat load to the reaction system, and then conducted again at 420° C. in the same manner as described above. It was confirmed that the yield of isophthalonitrile was still as high as 83.1 mol % after bearing heat load. Accordingly, it was recognized that when the recovered ammonia having a well-controlled water content was fed to the reaction system, the aimed product was stably produced at a high yield without change with time.

EXAMPLE 3

A mixed gas composed of 2.9% by volume of 3-methyl pyridine, 64.8% by volume of air and 32.3% by volume of recovered ammonia containing 25.0% by volume of water vapor, was charged into a reactor packed with the catalyst A, and then subjected to fluid catalytic reaction at a space velocity (SV) of 810 $Hr^{-1}$ and a temperature of 390° C. at which the maximum yield of 3-cyanopyridine was expected when using the catalyst A. The water content of the mixed gas fed to the reactor was 8.1% by volume. As a result of the reaction, it was confirmed that the initial yield of 3-cyanopyridine based on 3-methyl pyridine was 85.3 mol %. Then, the reaction was continued at 450° C. for 300 hours for applying a heat load to the reaction system, and then conducted again at 390° C. in the same manner as described above. It was confirmed that the yield of 3-cyanopyridine was still as high as 84.1 mol % after bearing heat load. Accordingly, it was recognized that when the recovered ammonia having a well-controlled water content was fed to the reaction system, the aimed product was stably produced at a high yield without change with time.

EXAMPLE 4

A mixed gas composed of 3.2% by volume of p-xylene, 71.5% by volume of air and 25.3% by volume of recovered ammonia containing 10.5% by volume of water, was charged into a reactor packed with the catalyst A, and reacted therein at 410° C. at which the maximum yield of terephthalonitrile was expected when using the catalyst A. The water content of the mixed gas fed to the reactor was 2.7% by volume. As a result of the reaction, it was confirmed that the initial yield of terephthalonitrile based on p-xylene was 88.2 mol %. Then, the reaction was continued at 450° C. for 300 hours for applying a heat load to the reaction system, and then conducted again at 410° C. in the same manner as described above. It was confirmed that the yield of terephthalonitrile was still as high as 87.77 mol % after bearing heat load. Accordingly, it was recognized that when the recovered ammonia having a well-controlled water content was recycled to the reaction system, the aimed product was stably produced at a high yield without change with time.

Preparation of Catalyst B:

The same procedure as used for the preparation of the catalyst A was performed except that sodium acetate was used instead of potassium acetate. The thus obtained catalyst contained as catalyst components, V, Cr, B, Mo, P and Na in such amounts that the atomic ratio of V:Cr:B:Mo:P:Na was 1:1:0.5:0.086:0.007:0.021. The concentration of the catalyst components in the obtained catalyst was 50% by weight. This catalyst is hereinafter referred to as "catalyst B".

EXAMPLE 5

A mixed gas composed of 3.2% by volume of m-xylene, 71.0% by volume of air and 25.8% by volume of recovered ammonia containing 5.2% by volume of water, was charged into a reactor filled with the catalyst B, and then subjected to fluid contact reaction at a space velocity (SV) of 850 $Hr^{-1}$ and a temperature of 420° C. at which the maximum yield of isophthalonitrile was expected when using the catalyst A, by the same method as in EXAMPLE 1. The water content of the mixed gas fed to the reactor was 1.3% by volume. As a result of the reaction, it was confirmed that the initial yield of isophthalonitrile based on m-xylene was 86.0 mol %. Then, the reaction was continued at 450° C. for 300 hours for applying a heat load to the reaction system, and then conducted again at 420° C. in the same manner as described above. It was confirmed that the yield of isophthalonitrile was still as high as 84.7 mol % after bearing heat load. Accordingly, it was recognized that when the recovered ammonia having a well-controlled water content was recycled to the reaction system, the aimed product was stably produced at a high yield without change with time.

Preparation of Catalyst C:

Nine hundreds milliliters of water was added to 700 ml of concentrated nitric acid, and the resultant solution was heated to 50 to 60° C. Then, 92 g of electrolytic iron was added to the solution and dissolved therein. The obtained solution was mixed with 1,460 g of 20-wt. % aqueous silica sol (containing 0.02% by weight of $Na_2O$) and then with 359 g of antimony trioxide ($Sb_2O_3$) and 39 g of boric acid ($H_3BO_3$). Further, a solution prepared by dissolving 2.53 g of potassium acetate ($CH_3COOK$) in 100 ml of water, was added to the resultant mixture. The obtained mixed solution was treated with 15% ammonia water to adjust the pH thereof to 2, and then aged at 100° C. for 3 hours. The resultant slurry was mixed with a chromium-containing solution prepared by dissolving 33 g of chromium nitrate nonahydrate ($Cr(NO_3)_3 \cdot 9 H_2O$) in 400 ml of water to obtain a slurry. Separately, 130 ml of water was added to 60 g of vanadium pentaoxide ($V_2O_5$), and the resultant mixture was heated to 80 to 90° C. Then, 125 g of oxalic acid was added to the mixture while intimately stirring to dissolve solids therein, thereby preparing a vanadyl oxalate solution. The vanadyl oxalate solution was added to the previously prepared slurry, and the mixture was intimately stirred to prepare a catalyst solution. The obtained catalyst solution was spray-dried while maintaining the inlet temperature at 250° C. and the outlet temperature at 130° C. The spray-dried catalyst was further dried within a dryer heated to 130° C. for 12 hours, pre-calcined at 400° C. for 0.5 hour, and then calcined at 800° C. for 8 hours under air stream. The obtained fluid catalyst had an alkali metal concentration of 0.21% by weight, and contained as catalyst components, Fe, Sb, V, Cr, B, Na and K in such amounts that the atomic ratio of Fe:Sb:V:Cr:B:Na:K was 1:1.5:0.4:0.5:0.77:0.011:0.031. The concentration of these catalyst components in the fluid catalyst is 50% by weight. The fluid catalyst was hereinafter referred to as "catalyst C".

EXAMPLE 6

A mixed gas composed of 3.2% by volume of m-xylene, 71.5% by volume of air and 25.5% by volume of the recovered ammonia containing 5.0% by volume of water, was fed into a reactor packed with the catalyst C, and then subjected to fluid catalytic reaction at a space velocity (SV) of 850 $Hr^{-1}$ and a temperature of 440° C. at which the maximum yield of isophthalonitrile was expected when using the catalyst C. The water content of the mixed gas fed to the reactor was 1.3% by volume. As a result of the reaction, it was confirmed that the initial yield of isophthalonitrile based on m-xylene was 79.8 mol %. Then, the reaction was continued at 450° C. for 300 hours for applying a heat load to the reaction system, and then conducted again at 440° C. in the same manner as described above. It was confirmed that the yield of isophthalonitrile was still as high as 79.7 mol % after bearing heat load. Accordingly, it was recognized that when the recovered ammonia having a well-controlled water content was recycled to the reaction system, the aimed product was stably produced at a high yield without change with time.

COMPARATIVE EXAMPLE 1

A mixed gas composed of 2.6% by volume of m-xylene, 57.6% by volume of air and 39.8% by volume of recovered ammonia containing 39.2% by volume of water, was fed into a reactor filled with the catalyst A, and then subjected to fluid catalytic reaction at a space velocity (SV) of 850 $Hr^{-1}$ and a temperature of 420° C. at which the maximum yield of isophthalonitrile was expected when using the catalyst A. The water content of the mixed gas fed to the reactor was 15.6% by volume. It was confirmed that the initial yield of isophthalonitrile based on m-xylene was 79.1 mol % after bearing heat load. Then, the reaction was continued at 450° C. for 300 hours for applying a heat load to the reaction system, and then conducted again at 420° C. in the same manner as described above. After completion of the reaction, it was confirmed that the yield of isophthalonitrile was reduced to 75.3 mol %. Accordingly, it was recognized that when the recovered ammonia having a high water content was recycled to the reaction system, the yield of isophthalonitrile as aimed product was lowered and considerably deteriorated with time.

COMPARATIVE EXAMPLE 2

A mixed gas composed of 2.6% by volume of 3-methyl pyridine, 60.1% by volume of air and 37.3% by volume of recovered ammonia containing 35.0% by volume of water, was fed into a reactor filled with the catalyst A, and then reacted at a space velocity (SV) of 810 $Hr^{-1}$ and a temperature of 390° C. at which the maximum yield of 3-cyanopyridine was expected when using the catalyst A. The water content of the mixed gas fed to the reactor was 13.0% by volume. As a result of the reaction, it was confirmed that the initial yield of 3-cyanopyridine based on 3-methyl pyridine was 80.1 mol %. Then, the reaction was continued at 450° C. for 300 hours for applying a heat load to the reaction system, and then conducted again at 390° C. in the same manner as described above. It was confirmed that the yield of 3-cyanopyridine was reduced to 75.3 mol % after bearing heat load. Accordingly, it was recognized that when the recovered ammonia having a high water content was recycled to the reaction system, the yield of 3-cyanopyridine as aimed product was lowered and considerably deteriorated with time.

COMPARATIVE EXAMPLE 3

A mixed gas composed of 2.7% by volume of p-xylene, 58.5% by volume of air and 37.8% by volume of recovered ammonia containing 40.1% by volume of water, was fed into a reactor filled with the catalyst A, and then subjected to fluid catalytic reaction at a space velocity (SV) of 850 Hr$^{-1}$ and a temperature of 410° C. at which the maximum yield of terephthalonitrile was expected when using the catalyst A. The water content of the mixed gas fed to the reactor was 15.2% by volume. As a result of the reaction, it was confirmed that the initial yield of terephthalonitrile based on p-xylene was 78.1 mol %. Then, the reaction was continued at 450° C. for 300 hours for applying a heat load to the reaction system, and then conducted again at 410° C. in the same manner as described above. It was confirmed that the yield of terephthalonitrile was reduced to 75.3 mol % after bearing heat load. Accordingly, it was recognized that when the recovered ammonia having a high water content was recycled to the reaction system, the yield of terephthalonitrile as aimed product was low and considerably reduced with time.

COMPARATIVE EXAMPLE 4

A mixed gas composed of 2.5% by volume of m-xylene, 56.9% by volume of air and 40.6% by volume of recovered ammonia containing 40.5% by volume of water, was fed into a reactor filled with the catalyst B, and then subjected to fluid catalytic reaction at a space velocity (SV) of 850 Hr$^{-1}$ and a temperature of 420° C. at which the maximum yield of isophthalonitrile was expected when using the catalyst B. The water content of the mixed gas fed to the reactor was 16.5% by volume. As a result of the reaction, it was confirmed that the initial yield of isophthalonitrile based on m-xylene was 76.7 mol %. Then, the reaction was continued at 450° C. for 300 hours for applying a heat load to the reaction system, and then conducted again at 420° C. in the same manner as described above. It was confirmed that the yield of isophthalonitrile was reduced to 71.3 mol % after bearing heat load. Accordingly, when the recovered ammonia whose water content was not controlled was recycled to the reaction system, the yield of isophthalonitrile as aimed product was low and considerably reduced with time.

COMPARATIVE EXAMPLE 5

A mixed gas composed of 2.5% by volume of m-xylene, 56.9% by volume of air and 40.6% by volume of recovered ammonia containing 40.5% by volume of water, was fed into a reactor filled with the catalyst C, and then subjected to fluid catalytic reaction at a space velocity (SV) of 850 Hr$^{-1}$ and a temperature of 440° C. at which the maximum yield of isophthalonitrile was expected when using the catalyst C. The water content of the mixed gas fed to the reactor was 16.4% by volume. It was confirmed that the initial yield of isophthalonitrile based on m-xylene was 76.7 mol % after bearing heat load. Then, the reaction was continued at 450° C. for 300 hours for applying a heat load to the reaction system, and then conducted again at 440° C. in the same manner as described above. After completion of the reaction, it was confirmed that the yield of isophthalonitrile was reduced to 72.3 mol %. Accordingly, it was recognized that when the recovered ammonia whose water content was not controlled was recycled to the reaction system, the yield of isophthalonitrile as aimed product was low and considerably reduced with time.

EXAMPLE 7

According to the flow diagram shown in FIG. 1, ammoxidation, separation of nitrile compounds and recovery of ammonia were conducted as follows.

Air, m-xylene (MX), fresh ammonia and an ammonia-containing gas from the ammonia regeneration tower D were mixed together, preheated to 350° C. and then charged into the ammoxidation reactor A filled with 6 liters of the catalyst A. As to the charging conditions, the flow rate of MX fed was 350 g/hr; the molar ratio of $NH_3$ to MX was 11; the molar ratio Of $O_2$ to MX was 5.4; and SV was 630 Hr$^{-1}$. The water content of the gas at an inlet of the reactor was 6.6% by volume, and the reaction was conducted at 420° C. under a pressure of 0.2 MPa.

The reaction product gas discharged from the top of the reactor was introduced into the nitrile separation tower B where nitrile compounds contained in the gas were dissolved in dimethylformamide (DMF) as a solvent to separate the nitrile compounds from the gas. Then, the residual gas discharged from the top of the nitrile separation tower B was introduced into the ammonia absorption tower C where ammonia, hydrogen cyanide, ammonium carbonate, etc., contained in the residual gas were dissolved in water. Waste gas discharged from the top of the ammonia absorption tower C and containing a carbon dioxide gas, carbon monoxide, nitrogen, oxygen, hydrogen cyanide and the like, was burned for disposal.

An aqueous solution discharged from the bottom of the ammonia absorption tower C was introduced into the ammonia regeneration tower D operated under a pressure of 0.3 MPa (bottom temperature: 133° C.). A mixed gas containing recovered unreacted ammonia, hydrogen cyanide, carbon dioxide gas, water vapor, etc., was separated at the top of the absorption tower, and recycled to the reaction system. Liquid bottom products discharged from the bottom of the ammonia absorption tower C were treated as waste water. The ammonia-containing mixed gas recovered at the top of the ammonia absorption tower C was composed of 73.6% of ammonia, 12.7% of carbon dioxide gas, 4.5% of hydrogen cyanide, 9.0% of $H_2O$ and the balance being inert gases. The yield of isophthalonitrile based on m-xylene was 83.4%. Also, liquid bottom products discharged from the bottom of the ammonia regeneration tower D contained 0.042% of formamide, 0.001% or less of formic acid and 4 ppm of hydrogen cyanide, and exhibited a TOD of 1,500 ppm and a coloration degree of 5 or less when expressed by Gardner color scale. The above operation was further continued for 9 days. As a result, it was confirmed that the differential pressure within the regeneration tower was kept constant, and the deterioration in heat transfer efficiency due to sticking of high-boiling substances or the like thereto was inhibited.

EXAMPLE 8

The procedure of EXAMPLE 7 was conducted for 11 days, and then the operation was continued in the same manner as in EXAMPLE 7 except that the pressure and temperature as operating conditions of the ammonia regeneration tower D were changed to 0.4 MPa and 144° C., respectively. As a result, it was confirmed that when the operation was in steady state, the water concentration of the gas at an inlet of the reactor was 5.1%, and the yield of isophthalonitrile based on m-xylene was 85.5%. Further, liquid bottom products discharged from the ammonia regeneration tower D contained 0.051% of formamide, 0.003% of formic acid and 4 ppm of hydrogen cyanide, and exhibited a TOD of 1,700 ppm and a coloration degree of 5 or less when expressed by Gardner color scale. Thereafter, the operation was further continued for 30 days. As a result, it was confirmed that the differential pressure within the ammonia regeneration tower D was kept constant, and the deterioration in heat transfer efficiency due to sticking of high-boiling substances or the like thereto was inhibited.

EXAMPLE 9

The ammoxidation of 3-methyl pyridine was conducted by the same method as in EXAMPLE 7. Specifically, the raw gas was fed into the ammoxidation reactor A under such charging conditions that the flow rate of 3-methyl pyridine was 300 g/hr; the molar ratio of $NH_3$ to 3-methyl pyridine was 5.6; the molar ratio of $O_2$ to 3-methyl pyridine was 2.8; the water content of the gas at an inlet of the reactor was 5.2%; and SV was 280 $Hr^{-1}$. The reaction temperature and pressure were set to 390° C. and 0.2 MPa, respectively.

The operating conditions of the nitrile separation tower B and ammonia absorption tower C were identical to those of EXAMPLE 6, and the operating pressure of the ammonia regeneration tower D and the bottom temperature thereof were set to 0.4 MPa and 142° C., respectively. When the operation was in steady state, the ammonia-containing gas recovered at the top of the ammonia regeneration tower D was composed of 77.7% of ammonia, 4.1% of hydrogen cyanide, 11.1% of carbon dioxide gas, 7.4% of $H_2$ O and the balance being inert gases. The yield of 3-cyanopyridine based on 3-methyl pyridine was 88.2%. Also, liquid bottom products discharged from the bottom of the regeneration tower, contained 0.05% of formamide, 0.007% of formic acid and 3 ppm of hydrogen cyanide, and exhibited a TOD of 1,700 ppm and a coloration degree of 5 or less when expressed by Gardner color scale. The above operation was further continued for 30 days. As a result, it was confirmed that the differential pressure within the regeneration tower was kept constant, and the deterioration in heat transfer efficiency due to sticking of high-boiling substances or the like thereto was inhibited.

COMPARATIVE EXAMPLE 6

The ammoxidation of m-xylene was conducted by the same method as in EXAMPLE 7. In the ammoxidation, the ammonia regeneration tower D was operated under the same conditions as in EXAMPLE 7 except that the operating pressure and bottom temperature thereof were changed to 0.8 MPa and 172° C., respectively. When the operation was continuously conducted under the above conditions, the differential pressure within the ammonia regeneration tower D was fluctuated with time, so that downcomer flooding frequently occurred, and it became difficult to conduct a stable operation. When the operation was in steady state, the water concentration of the gas at an inlet of the ammoidation reactor A was 3.1%, and the yield of isophthalonitrile based on m-xylene was 86.2%. Also, liquid bottom products discharged from the bottom of the ammonia regeneration tower D, contained 0.482% of formamide, 0.166% of formic acid and 4 ppm of hydrogen cyanide, and exhibited a TOD of 6,800 ppm and a coloration degree of 18 or more when expressed by Gardner color scale. Thereafter, the above operation was further continued for 7 days. As a result, a remarkable deterioration in heat transfer efficiency was confirmed since the overall coefficient of heat transfer thereof was reduced to a half value.

COMPARATIVE EXAMPLE 7

The ammoxidation of m-xylene was conducted by the same method as in EXAMPLE 7. In the ammoxidation, the ammonia regeneration tower D was operated under the same conditions as in EXAMPLE 7 except that the operating pressure and bottom temperature thereof were changed to 0.15 MPa and 118° C., respectively. After initiation of the operation, the water concentration of the gas at an inlet of the ammoxidation reactor A was gradually increased and reached 10.5% by volume. The yield of isophthalonitrile based on m-xylene was 79.2%. Thereafter, the above operation was further continued. As a result, the temperature of stream at the top of regeneration tower was reduced to 82° C. or lower, and ammonium carbonate was precipitated in the reflux vessel. Therefore, since stable operation became difficult due to these defects, the operation was stopped.

What is claimed is:

1. A process for producing a nitrile compounds by ammoxidation of a carbocyclic or heterocyclic compound having organic substituent(s) in which said compound was reacted with ammonia and an oxygen-containing gas, comprising:

conducting the ammoxidation by vapor-phase catalytic reaction in the presence of a fluid catalyst containing at least one metal oxide selected from the group consisting of vanadium oxide, molybdenum oxide and iron oxide while controlling a water content of a gas fed to a reactor to 12% by volume or lower;

recovering unreacted ammonia from a reaction product gas obtained by the ammoxidation; and recycling the recovered ammonia to the reaction system.

2. The process according to claim 1, wherein said catalyst comprises metal oxides containing (i) at least one element selected from the group consisting of V, Mo and Fe, and (ii) at least one element selected from the group consisting of Mg, Ca, Ba, La, Ti, Zr, Cr, W, Co, Ni, B, Al, Ge, Sn, Pb, P, Sb, Bi, Li, Na, K, Rb and Cs, and silica on which said metal oxides are supported.

3. The process according to claim 2, wherein said catalyst comprises metal oxides of V, Cr, B, Mo and P, and alkali metal which are supported on silica.

4. A process for producing a nitrile compounds by ammoxidation of a carbocyclic or heterocyclic compound having organic substituent(s) in which said compound is reacted with ammonia and an oxygen-containing gas, comprising:

separating the nitrile compounds from a reaction product gas obtained by the ammoxidation;

absorbing unreacted ammonia and by-produced hydrogen cyanide present in the residual gas, in water;

distilling the obtained solution under a pressure of 0.2 to 0.7 MPa to recover the ammonia and hydrogen cyanide therefrom; and recycling the recovered ammonia and hydrogen cyanide to reaction system.

5. The process according to claim 4, wherein said nitrile compounds is separated from the reaction product gas by contacting the gas with an organic solvent to absorb the nitrile compounds therein.

6. The process according to claim 4, wherein said nitrile compounds is separated from the reaction product gas by cooling the gas to crystallize the nitrile compounds.

7. The process according to claim 4, wherein the liquid residence time in a distilling apparatus used for recovery of ammonia and hydrogen cyanide, is in the range of 0.1 to 2.0 hours.

8. The process according to claim 4, wherein the water content of a gas fed to a reactor is 12% by volume or lower.

9. The process according to claim 4, wherein the vapor-phase catalytic ammoxidation is conducted using a fluid catalyst containing at least one metal oxide selected from the group consisting of vanadium oxide, molybdenum oxide and iron oxide.

10. The process according to claim 9, wherein said catalyst comprises metal oxides containing (i) at least one element selected from the group consisting of V, Mo and Fe, and (ii) at least one element selected from the group consisting of Mg, Ca, Ba, La, Ti, Zr, Cr, W, Co, Ni, B, Al, Ge, Sn, Pb, P, Sb, Bi, Li, Na, K, Rb and Cs, and silica on which said metal oxides are supported.

11. The process according to claim 10, wherein said catalyst comprises metal oxides of V, Cr, B, Mo and P, and alkali metal which are supported on silica.

* * * * *